(12) United States Patent
Trueba et al.

(10) Patent No.: US 6,698,868 B2
(45) Date of Patent: Mar. 2, 2004

(54) THERMAL DROP GENERATOR FOR ULTRA-SMALL DROPLETS

(75) Inventors: Kenneth E. Trueba, Philomath, OR (US); Charles C. Haluzak, Corvallis, OR (US); Terry E. McMahon, Albany, OR (US); Donald W. Schulte, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 56 days.

(21) Appl. No.: 10/000,425

(22) Filed: Oct. 31, 2001

(65) Prior Publication Data

US 2003/0081072 A1 May 1, 2003

(51) Int. Cl.[7] .................................................. B41J 2/05
(52) U.S. Cl. .......................................... 347/63; 347/65
(58) Field of Search ............................. 347/20, 44, 45, 347/56, 61, 47, 63, 65, 107

(56) References Cited

U.S. PATENT DOCUMENTS

| 5,478,606 | A | | 12/1995 | Ohkuma | 427/555 |
|---|---|---|---|---|---|
| 5,894,841 | A | | 4/1999 | Voges | 128/203.12 |
| 6,036,874 | A | | 3/2000 | Farnaam | 216/27 |
| 6,113,221 | A | | 9/2000 | Weber | 347/61 |
| 6,137,443 | A | * | 10/2000 | Beatty et al. | 347/63 |

FOREIGN PATENT DOCUMENTS

| DE | 19536429 | 4/1997 | |
|---|---|---|---|
| EP | 0244214 | 4/1987 | |
| EP | 0 783 970 | 6/1997 | B41J/2/16 |
| EP | 0783970 | 7/1997 | |
| EP | 0 814 380 | 12/1997 | B41J/2/16 |
| JP | 5995156 | 10/1984 | |
| JP | 610098557 | 5/1986 | |
| JP | 62094347 | 4/1987 | |
| JP | 40052144 | 2/1992 | |

* cited by examiner

*Primary Examiner*—Juanita Stephens

(57) ABSTRACT

A thermal-type drop generator for ejecting droplets of liquid having ultra-small volumes. In one embodiment the drop generator includes a chamber defined in part by an orifice member. The chamber is supported by a rigid substrate. Removable material is used in fabricating the chamber.

9 Claims, 3 Drawing Sheets

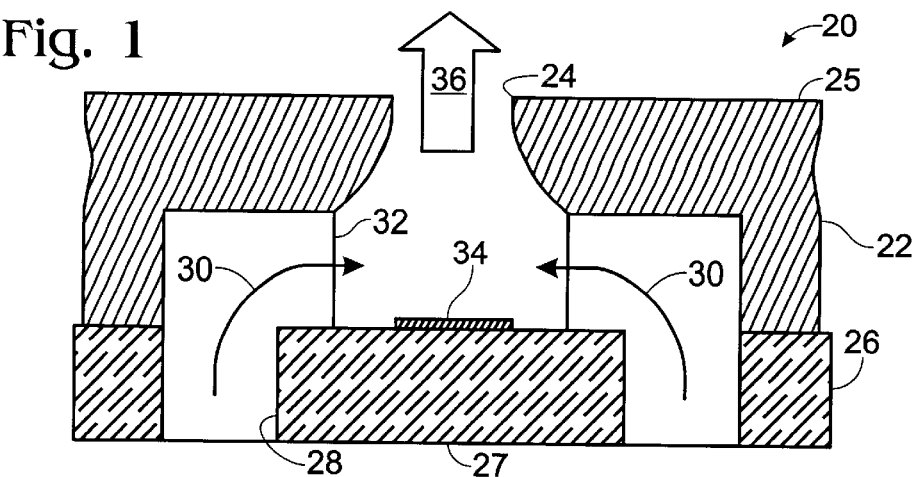
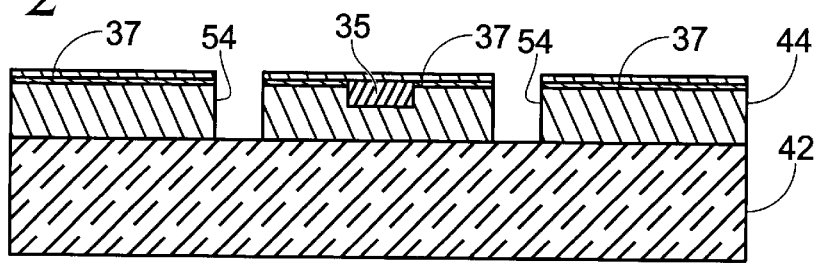
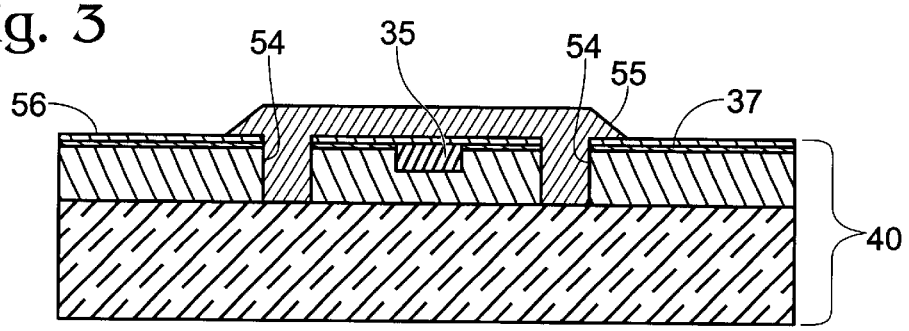
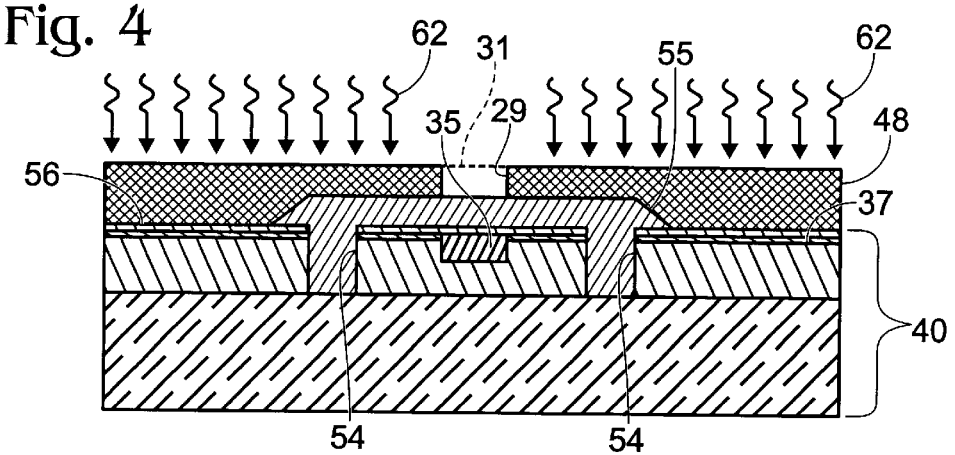

US 6,698,868 B2

THERMAL DROP GENERATOR FOR ULTRA-SMALL DROPLETS

TECHNICAL FIELD

This invention relates to the generation of ultra-small liquid droplets. Droplets having volumes ranging in the tens of femtoliters are characterized here as ultra-small.

BACKGROUND OF THE INVENTION

The ongoing advances in medicine and biotechnology are providing many effective and promising systemic therapies that call for the delivery of biological and chemical substances (such as peptides, proteins, and small molecules) to a patient's bloodstream. There are various problems associated with getting certain substances to the bloodstream by conventional delivery means, such as transdermal and oral. For instance, oral delivery of therapeutic proteins does not work because the proteins are digested before they have an opportunity to reach the bloodstream. Thus, for this and other reasons, it is best to deliver such substances to the bloodstream by as direct a route as possible.

An aerosol is a gaseous suspension of very fine solid or liquid particles. Aerosols are presently used for delivering certain drugs to a patient's lungs. Delivery of drugs or other therapeutic substances to a patient's lungs is sometimes referred to as pulmonary delivery.

The innermost tissue of the lung is known as the alveolar epithelium, which comprises hundreds of millions of tiny air sacs, called alveoli, that are surrounded by a large network of blood capillaries. The alveoli enable rapid absorption of fluids from the alveoli to the bloodstream. Most effective pulmonary delivery is accomplished when the substance is delivered to the alveoli. The delivery process requires the generation of very small particles or droplets that can be entrained in a gas as an aerosol and inhaled by the patient into the alveoli for transfer to the bloodstream.

The lung's alveoli can readily absorb liquid drops having diameters equal to or less than about 4 $\mu$m, which represents a volume of about 33 femtoliters. A femtoliter is one quadrillionth ($10^{-15}$) of a liter. Larger drops tend to contact the lung walls before reaching the alveoli and are less likely to permeate the wall to the bloodstream because the airway to the alveoli is lined with a thick, ciliated mucus-covered cell layer.

A popular pulmonary delivery mechanism is known as a metered dose inhaler (MDI). These are widely used for the delivery of asthma medication. While an MDI delivery system may be effective for medications designed to medicate the lung tissue, they are not optimal for delivery of substances to the alveoli (hence, to the bloodstream). In this regard, an MDI typically combines the drug with a propellant in a pressurized container. Actuation of the device releases metered doses of the aerosol, but the droplet size distribution is large, and the vapor pressure of the propellant varies with temperature and number of uses. Thus, the behavior of the material in the air stream and the extent to which droplets reach the alveoli becomes somewhat unpredictable.

In view of the foregoing, it can be appreciated that there is a need for a droplet generator that can reliably produce ultra-small-volume droplets with a generally uniform size distribution for entrainment in aerosols.

There exists the potential for generating very small droplets using a drop generator that is adapted from the kind employed in ink-jet printing. The type of ink-jet printing of interest here (often called thermal ink-jet printing) conducts ink into tiny chambers. Each chamber includes a heat transducer such as, for example, a thin-film resistor, to create a vapor bubble that ejects a droplet of ink through an orifice that overlies the chamber. The chambers and orifices are incorporated into a printhead device that is connected with a supply of ink and with a controller for timing the droplet ejection to reproduce images on media.

Current ink-jet designs provide drop generators that produce droplet volumes as small as about 4 picoliters, which is equivalent to 4,000 femtoliters. In order to produce droplets in the range of tens of femtoliters that, for example, can be entrained in an aerosol for delivery of the droplets to the alveoli, one is confronted with several problems that prevent a simple scaling-down of current designs to arrive at such ultra-small droplet volumes.

For example, ejection of single droplets in the tens of femtoliters size range requires extremely small liquid chambers that have critical dimensions that must be carefully controlled during the fabrication process.

SUMMARY OF THE INVENTION

The present invention is directed to the manufacture and use of a thermal-type drop generator for ejecting droplets of liquid having ultra-small volumes. In one preferred embodiment of the present invention the drop generator includes an ultra-small liquid chamber defined in part by an orifice member. Removable material is used in fabricating the chamber. The material is sized to match the chamber shape, and it supports the orifice member during processing of the material that makes up the orifice member. The use of such removable material is one of the features of the present invention for producing a drop generator for ejecting the ultra-small droplets.

Methods and apparatus for carrying out the invention are described in detail below. Other advantages and features of the present invention will become clear upon review of the following portions of this specification and the drawings.

BRIEF DESCRIPTION OF THE DRAWINGS

FIG. 1 is a reproduction of a graphic taken from a computational fluid dynamics simulation of the performance of a drop generator configured in accordance with the present invention.

FIGS. 2–5 are enlarged cross sectional views of the steps of fabricating a representative drop generator embodiment in accordance with the present invention.

DETAILED DESCRIPTION OF THE PREFERRED EMBODIMENT

Figure 5:
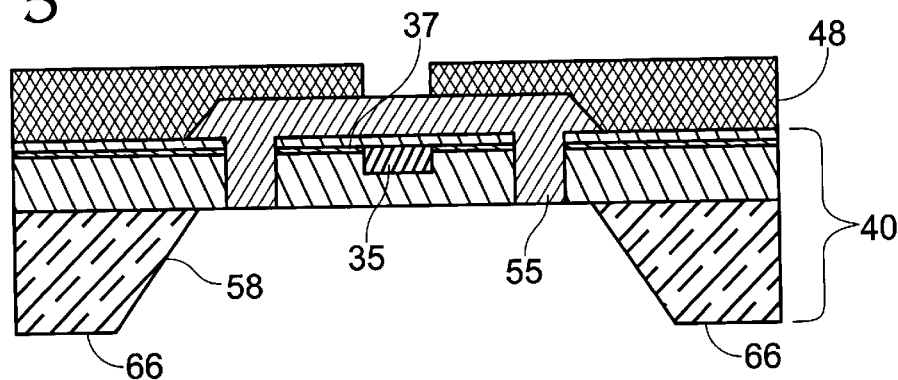

FIG. 1 is a reproduction of a graphic taken from a computational fluid dynamics simulation of the performance of a drop generator that is formed in accordance with one aspect of the present invention. In that figure, the drop generator 20 is depicted in cross section. For modeling purposes, a solid orifice structure 22 is constructed as a generally planar member having a circular orifice 24 defined in it. The orifice 24 has a minimum diameter of about 2 micrometers ($\mu$m) at the surface 25 of the orifice structure 22. The orifice diameter gradually increases in the inward direction as shown in FIG. 1. The orifice shape need not be restricted to being circular. Other near-circular shapes will suffice and are contemplated, preferably with the minimum dimension of the orifice being 2 $\mu$m across.

The orifice structure is continuous with a solid substrate member 26 that underlies the orifice structure and has its opposing side 27 in communication with a liquid. Two inlets 28 are defined in the substrate to allow the liquid to flow (as depicted by arrows 30) into a chamber 32. The chamber 32 is a small reservoir for holding liquid prior to ejection of the liquid from the chamber through the orifice 24.

The mechanism for ejecting the liquid from the chamber is the generation of a vapor bubble in the chamber by a heat transducer 34 that is inside the liquid-filled chamber. The rapid expansion of the bubble ejects the liquid. For computational purposes the heat transducer 34 is considered a planar member (such as a thin-film resistor) that, upon actuation, provides an energy density of about 0.014 mJ/$\mu$m$^2$. The liquid under consideration has a viscosity of about 3 cp and a boiling point of 100° C.

In accordance with the present invention, a droplet having a volume in the range of 10 femtoliters is ejected from the chamber, along a trajectory as shown by arrow 36, upon activation of the heat transducer 34. In one implementation of this invention, the volume of the chamber for producing the ultra-small droplets is only slightly larger than the droplets themselves. The fabrication of such drop generators having ultra-small chamber volumes must be carefully controlled to ensure that the generators can be reliably reproduced. This is especially important with respect to maintaining the shape and size of the chamber during fabrication of the drop generator. What follows is a description of one preferred approach to fabricating drop generators in accordance with the present invention.

Figure 6:
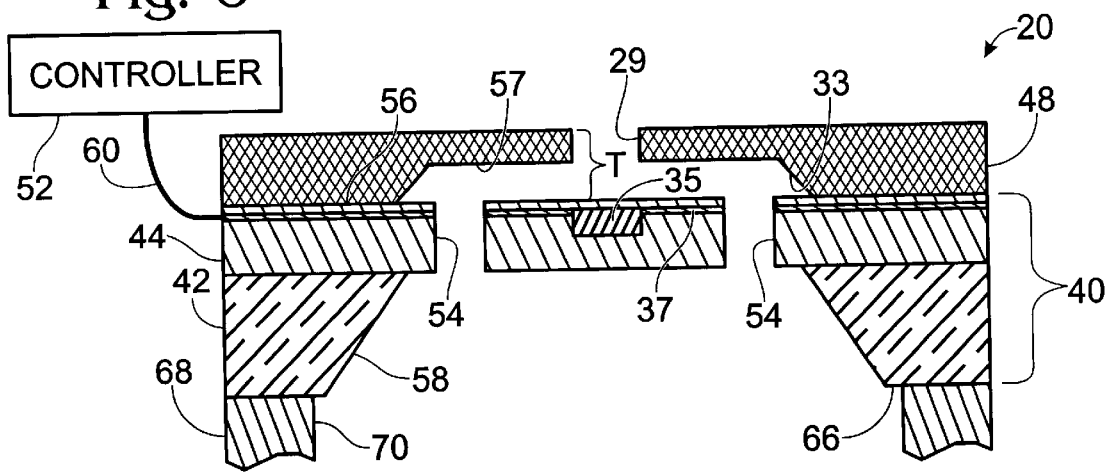
FIG. 6 is an enlarged cross section diagramming a completed drop generator embodiment.

FIG. 6 shows a greatly enlarged cross section of one drop generator 20 formed in accordance with the present invention. For illustrative purposes only one drop generator is shown, but, as will become clear, the fabrication process allows the production of multiple drop generators. The number of drop generators produced depends upon the amount of droplets that are required for a given application. One can consider this requirement in terms of flux, or the number of droplets that are simultaneously ejected from the drop generators. For greater flux requirements, more drop generators can be fabricated. For example, an array of 9000 drop generators operating at 200 kHz could be employed for producing droplets at a volumetric rate of about 25 microliters per second.

The exemplary drop generator 20 includes a rigid substrate 40 that can be a silicon base 42, which is preferably a conventional silicon wafer upon which has been grown an insulation layer, such as silicon dioxide. The substrate 40 may be as described in the prior art relating to ink-jet printing, an example of such art being U.S. Pat. No. 4,719,477. The substrate includes a layer of resistive material, such as tantalum aluminum portions 35 that are individually connected by thin conductors 37 that are patterned from a conductive layer. These conductors 37 are connected to traces on a flex circuit 60 (shown diagrammatically in FIG. 6). That circuit connects with a controller 52 for operating the drop generators as described more fully below.

The individual portions 35 of the resistive layer (FIG. 6), hereafter referred to as heat transducers or resistors, are part of what may be collectively referred to as the control layer 44 of the substrate 40, which includes the insulating layer of silicon dioxide, a resistor-protective passivation, and other sub-layers as described, for example, in U.S. Pat. No. 4,719,477. The requirement for a passivation layer may be minimal in instances where the liquid to be ejected from the chamber is not damaging to the resistor. In any event, the present invention may be incorporated with any of a number of planar, thermal transducer substrate configurations.

The substrate 40 may incorporate CMOS circuit components for permitting the use of multiplexed control signals for firing the drop generators. This simplifies the connection with the heat transducers 35 (that is, eliminates the need for numerous traces directly connected with the heat transducers). Also, the complex control logic afforded by the CMOS circuitry enables, for example, precise metering requirements to be programmed into that circuit and, thus, carried with a device (such as an inhaler) for which the drop generators are fabricated. For instance, if medicinal fluid droplets are to be ejected for an aerosol treatment that requires gradually increasing dosage, the control circuitry can be programmed to fire additional drop generators (increase the flux) with each subsequent use of the device.

With continued reference to the completed drop generator illustrated in FIG. 6, a unitary orifice member 48 is affixed to the control layer 44 and is shaped to define for each drop generator an orifice 29 and underlying liquid chamber 33 that is continuous with the orifice. The resistor 35 is selectively driven (heated) with a pulse of electrical current delivered by the conductors 37. (The conductors bypass the hereafter-described inlets 54.) The heat from the resistor is sufficient to vaporize some of the liquid in the chamber 33, thereby forcing the liquid through the orifice 29 in the form of a droplet as described above with respect to FIG. 1.

Each chamber 33 is refilled after each ejection with liquid that flows into the chamber through inlets 54 that are formed through the control layer 44. In a preferred embodiment, the upper surface 56 of the control layer 44 of the substrate is patterned and etched to form the inlets 54 before the orifice member 48 is attached to the substrate, and before a channel 58 is etched in the base 42 of the substrate 40, as described below. (The surface 56 is named "upper" for convenience and with the understanding that the surface 56 may be oriented beneath the remainder of the control layer 44 when the drop generator is inverted from the orientation shown in FIG. 6.)

The particulars of the fabrication steps of the drop generator 20 are described with reference to FIG. 2. Shown there is substrate base 42 after it has been processed to carry the control layer 44 that includes the previously formed inlets 54.

FIG. 3 illustrates the substrate 40 after formation of a removable mandrel 55 that temporarily fills the inlets 54 and is shaped to define the final shape of the chamber 33 as shown in FIG. 6). As will be described, the ultra-small chamber volume is defined in part with a photoresist material that is exposed to form the orifice member 48 (FIG. 6). The use of a mandrel, such as depicted at 55 in FIG. 3, helps to ensure that the resulting orifice member will be a substantially planar member having a predictable thickness "T" (FIG. 6), which ensures that the correct chamber volume is in place for the desired ultra-small-volume drop generator.

Put another way, in the absence of the use of a mandrel in accordance with the present invention, the normal erosion and slight deformation of photoresist material that occurs in the course of exposing portions of that material (which erosion may not affect larger-scale drop generator fabrications) will result in unacceptably larger orifices and smaller liquid chambers than desired when ultra-small chamber volumes are sought. That is, in working with ultra-small chamber volumes, the photoresist fabrication approach does not provide the fabrication tolerances required for such small chambers. The use of the mandrel or the present invention supports the photoresist material in a manner that reduces erosion and deformation of that material during processing of the orifice member, thereby providing a more predictable final chamber and orifice size.

As will become clear upon reading this description, in one sense the use of a removable mandrel 55 is akin to a lost-wax method of casting whereby replaceable material, wax, is used to support and define the shape of an outer structure (such as a mold) that is built around the wax. The wax is removed once the mold is complete.

In one preferred embodiment the mandrel is comprised of spin-on glass (SOG) material, which can be a mixture of silicon dioxide suspended in a solvent solution with dopants such as boron or phosphorous, preferably phosphorous. Alternatively, the SOG may be a siloxene-type, which is a Si—O polymer with attached methyl groups. The SOG is applied using conventional spin coating techniques, filling the inlets 54 and built up to a thickness matching the height of the chamber 33 between the upper surface 56 of the control layer 44 and what will become the underside 57 of the orifice member 48 at the orifice 29 (see FIG. 6).

The SOG is thereafter patterned to define the chamber shape and portions outside of that shape are etched away using, for example, HF, to leave the mandrel 55 configuration illustrated in FIG. 3. The SOG material helps to maintain the planarity of the surfaces of the later-applied and processed orifice member 48. Also, the SOG material is advantageous because it adheres well to the orifice member material, which is described below.

In an alternative embodiment the mandrel could be made from metal, such as aluminum, applied and shaped using conventional metal deposition and etching (wet or dry) techniques.

With the removable mandrel in place, the orifice member 48 is applied to the upper surface 56 of the substrate, across the area of the mandrel 55 (FIG. 4). In one preferred embodiment, the orifice member is a slow-cross-linking polymer that is applied using a conventional spin-coating tool such as one manufactured by Karl Suss, KG. In a preferred embodiment, the photoresist material comprises a photo-polymerizable epoxy resin known generally in the trade as SU-8. One example is that available from Micro-Chem Corp. of Newton, Mass. and sold under the name of SU8–10. It will be appreciated, however, that the orifice member could comprise any of a number of photoresist materials that become insoluble in developing solutions after exposure to electromagnetic radiation, such as UV radiation.

The spin-coating process associated with the spin-coating tool allows a planar surface to be formed as the slow-cross-linking polymer covers the mandrel 55. An exemplary process for spin coating is to spread a layer of the resist onto a substrate wafer (which carries a plurality of mandrels for forming an associated plurality of drop generators) with the spin coating tool set to 70 rpm with an acceleration of 100 rpm/s and a spread time of 20 seconds. The spinning is then stopped with a deceleration of 100 rpm/s and rest for 10 secs. The coated substrate is then spun at 1060 rpm at an acceleration rate of 300 rpm/s for 30 secs to spread the resist over the entire substrate.

Alternative polymer application processes can be used, including roll coating, curtain coating, extrusion coating, spray coating, and dip coating. Those skilled in the art will appreciate that there exist other methods to apply the polymer layers to the substrate. The slow cross-linking polymer is made by mixing optical dye (such as orange #3, ~2% weight) into either a photoimagable polyimide or photoimagable epoxy transparent polymer material. By adding dye, the amount of electromagnetic energy required is greater than non-dye mixed material to cross-link the material.

FIG. 4 illustrates the exposure of the layer of the cross-linking polymer material of member 48 with a high dosage of electromagnetic energy (illustrated with arrows 62). In an exemplary embodiment, this step is carried out with a Micralign scanning projection aligner as manufactured by SVG of San Jose, Calif., with an exposure setting that is sufficient to expose and cross link the entire depth of the orifice member polymer.

The energy (such as UV radiation) is applied to the orifice member material through a mask (not shown). The mask is a conventional device comprising, for example, a quartz substrate patterned with opaque material such as chromium to define (by leaving unexposed) the shape of the orifice 29. The unexposed portion of the polymer that represents the orifice 29 (shown at dashed line 31 in FIG. 4) is then removed using, for example, a process comprising a 70-second development in N-methyl-2-pyrrolidinone (NMP) at 1 krpm and an 8 second mix of isopropyl alcohol (IPA) and NMP at 1 krpm, then a 10-second rinse with IPA at 1 krpm, and, finally, a 60 second spin at 2 krpm. Such a developing tool is available from Solitec Wafer Processing, Inc., of San Jose, Calif.

FIG. 5 shows the drop generator upon the completion of the orifice member development step. The underside 66 of the substrate is then etched with a silicon etch, such as tetramethyl ammonium hydroxide (TMAH) to create the channel 58. The channel 58 is intended for fluid communication with the inlets 54 as explained below.

At the time or subsequent to the creation of the channel 58 in the substrate base 42, the mandrel 55 is removed. In the embodiment using the SOG material, an HF etch can be carried out on both sides of the substrate for removing the mandrel to arrive at the configuration shown in FIG. 6. Other mandrel materials would require suitable etchants for removing the mandrel.

In a preferred embodiment, the height of the chamber 33 (that is, between the top surface 56 of the control layer and the underside 57 of the orifice member covering the chamber is selected to be about 2 $\mu$m. Any of a number of chamber shapes (rounded or rectilinear walls) will suffice. In the preferred embodiment, the overall chamber volume is 25 femtoliters. This volume can be considered as the volumetric portion of the chamber over the resistor 35 as well as the volume of the orifice 29. A chamber of this overall volume and an associated resistor having an area of about 9 $\mu m^2$ will produce a droplet having a volume in the range of 10 femtoliters. Of course, one of ordinary skill in the art will understand that the viscosity of the liquid and other factors will affect drop volume. The foregoing dimensions relate to a liquid having a viscosity of about 3 cp and a boiling point of 100° C.

A supply of liquid may be provided to the substrate channel 58 in any of a number of ways. For example, the substrate undersurface 66 may be attached to the outer surface of a body 68 of a device (FIG. 6) that carries a reservoir of liquid. The body surface is configured with several conduits 70 (one of which is shown in FIG. 6), each conduit 70 aligning with a channel 58 for directing the liquid from a reservoir to the channel. As noted above, a substrate can carry many drop generators 20, several of which can be fluidically coupled to the linear channel 58 in the substrate, and the substrate can carry several of such channels.

Figure 7:
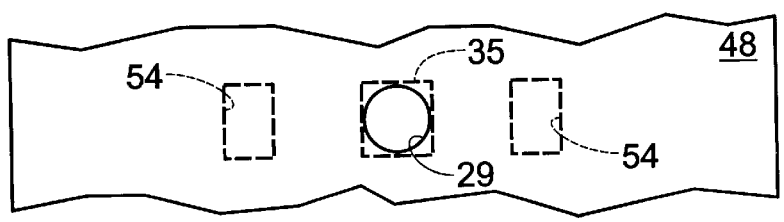
FIG. 7 is a top plan view of the embodiment shown in FIG. 6.

FIG. 7, shows in a top plan diagram the arrangement of the exemplary orifice 29, resistor 35, and inlets 54 of the embodiment of FIG. 6. There, liquid flows from the channel 58 (FIG. 6) into two inlets 54 disposed on opposite sides of the resistor 35. It may be desirable to alter this arrangement so that only a single inlet 54 is provided on one side of the resistor.

Figure 8:
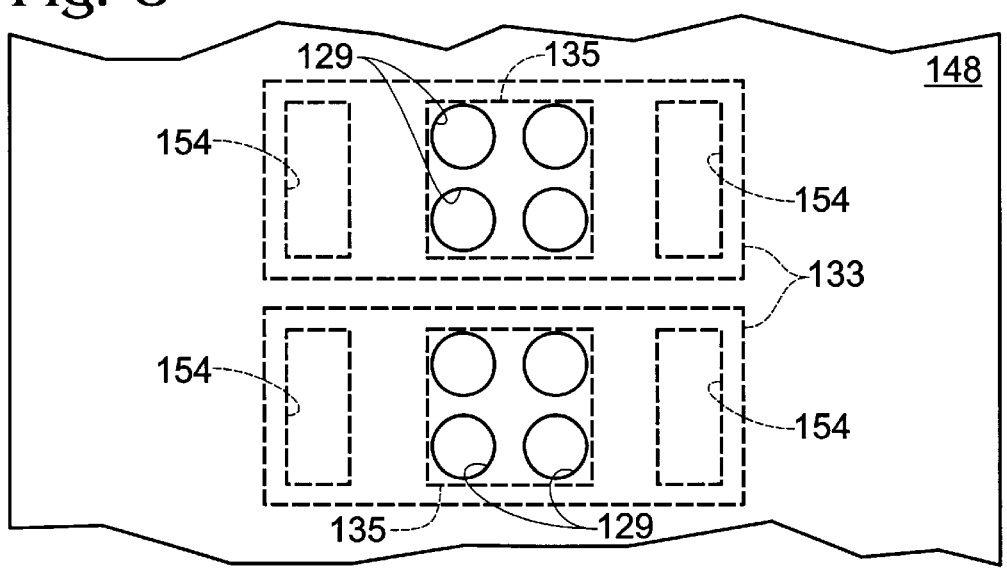
FIG. 8 is a top plan view showing an alternative embodiment of the invention.

FIG. 8 shows in a top plan diagram an alternative arrangement of orifice, resistor, and inlet components of an exemplary pair of chambers 133 as formed in accordance with the present invention. Here, a relatively large resistor 135 (for example, 6 $\mu m^2$) is used and the orifice member 148 is formed with four orifices 129 overlying the four corner portions of the resistor. The liquid provided to the resistor 135 flows through a pair of inlets 154, one inlet on each side of the resistor 135.

Figure 9:
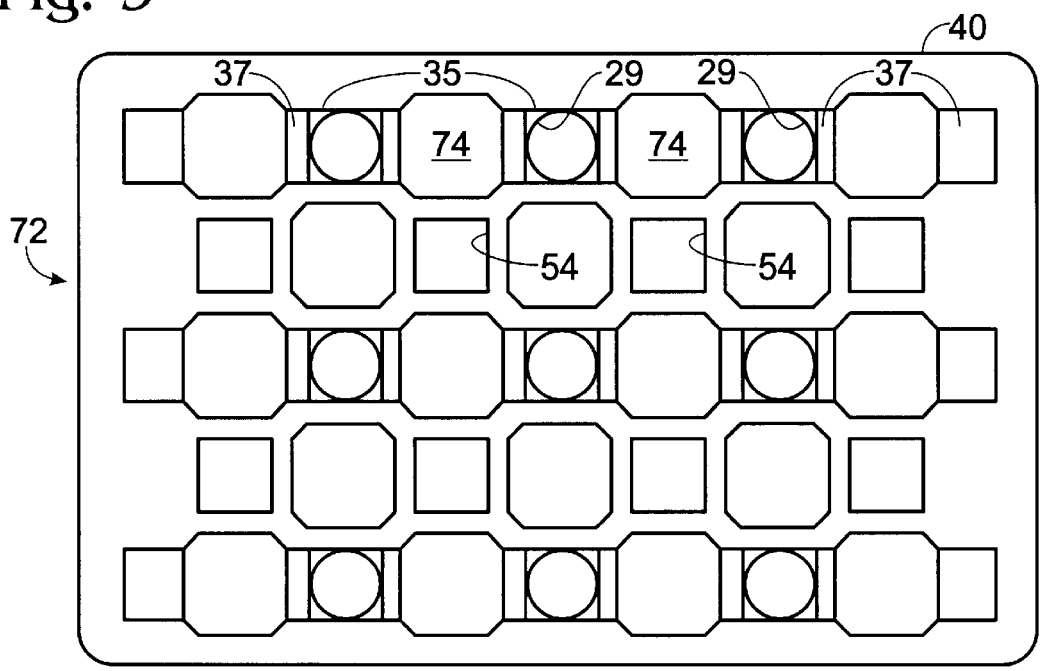
FIG. 9 is a diagram illustrating one preferred arrangement of an array of drop generators formed in accordance with the present invention.

FIG. 9 is a diagram for illustrating yet another one of several ways of arranging a small group of drop generators on a substrate 40 (the drop generators being made in a batch following the process steps set forth above). This overall device (substrate with multiple drop generators) can be considered a drop generator head 72. The diagram of FIG. 9 is a plan view wherein the circular items represent the array of orifices 29 that are above the resistors 35. The resistors 35 are connected by the conductive layers 37 that extend to a location near the edges of the substrate 40 for connection with the above-mentioned circuit 60 that leads from the controller.

In the embodiment of FIG. 9, the orifice member 48 is formed to extend between the upper surface 56 of the control layer 44 (see FIG. 6) in the regions away from the orifices, thereby to define barrier islands 74 as shown in FIG. 9 for supporting the orifice member on the control layer 44. Thus, the chambers 33 are generally contiguous with one another. Also, in this embodiment, the inlets 54 are square in cross section and arranged so that there are at least two inlets 54 adjacent to each resistor 35.

Other arrangements are contemplated. For example, the resistors and orifices need not be aligned in a 90-degree grid as shown in FIG. 9. Rather, the resistors and orifices can be arranged in staggered columns and/or rows.

As mentioned above, the present invention provides a drop generator for creating droplets having volumes in the range of tens of femtoliters and that, for example, are suitable for entrainment in an aerosol for effective pulmonary delivery. For instance, the drop generator head 72 may be mounted to receive a medicinal liquid (or any liquid-based biological and chemical substances as mentioned above).

Even though the foregoing description has focused on the production of ultra-small droplets suitable for aerosol delivery to the alveoli, it will be appreciated that such small droplets can be generated for other applications. Of course, the drop generators may be used for ejecting ultra-small droplets of ink to enable ink-jet printing with remarkably high resolution. The drop generators of the present invention also could be incorporated with supplies of liquids suitable for scent delivery, or dispensing precisely controlled amounts of pesticides, paints, fuels, etc. It is also contemplated that such drop generators may be employed in microfabrication processes like the ones contemplated in this description. For example, ultra-small mandrel-like or other features may be formed using such drop generators to deposit liquid-based material to a substrate for further curing or other processing.

Having here described preferred embodiments of the present invention, it is anticipated that other modifications may be made thereto within the scope of the invention by individuals skilled in the art. For example, the mandrel material may be selected to be heavily dyed (as compared to the orifice member material) photo-polymerizable epoxy such that exposure to the radiation that cross-links the orifice member will not do the same to the mandrel material. Thus the polymer mandrel can be dissolved for removing the mandrel after the orifice material is completely formed.

In one embodiment, the mandrel material and orifice member material are selected to provide a wetting characteristic of the orifice member material such that it wets (i.e., has a contact angle of less than 90 degrees) the surface of the mandrel to which it is applied. This wetting characteristic ensures that the interface between the removable mandrel and the orifice member is continuous and free from air bubbles and other irregularities that may occur if the orifice member material was non-wetting as respects the mandrel. Moreover, the mandrel material may be selected (or surface treated) so that after that material is removed from the chamber 33 there remains a residue on the chamber surface that enhances the wetting characteristic of the chamber surface. This will improve liquid flow into and out of the chamber and reduce the likelihood of entrapping air in the chamber.

Also, it is also contemplated that the mandrel material may be shaped to include the cylindrical portion that defines each orifice (as shown at dashed line 31 in FIG. 4, so that the orifice material, such as the described SU-8 or any other suitable orifice material, may be spun-on and exposed without the need to pattern separately the individual orifice portions. In this case, the use of a chemical-mechanical polishing (CMP) step would be required for planarizing the orifice material surface and ensuring no orifice material overlies the cylindrical portion 31 before the next process step (removal of the mandrel material) is undertaken.

Moreover it is contemplated that before the control layer 44 is fabricated on the silicon base 42, the surface of the base that carries the control layer 44 can be etched to define a recess. The recess is filled with polysilicon, the surface of which is made planar (as by chemical-mechanical polishing) with that of the adjacent surface of the base. The polysilicon material underlies the control layer 44, including resistive portion 35, in the space between and surrounding the inlets 54. The polysilicon makes more durable the portion of the drop generator that spans the channel 58 shown in FIG. 6.

Thus, although preferred and alternative embodiments of the present invention have been described, it will be appreciated that the spirit and scope of the invention is not limited to those embodiments, but extend to the various modifications and equivalents as defined in the appended claims.

What is claimed is:

1. An assembly for producing a drop generator that has a fluid chamber having a chamber shape for holding ultra-small volumes of fluid, wherein the drop generator includes an orifice member that substantially covers the chamber and that has an orifice therethrough, comprising:

a substrate; and a removable mandrel disposed on the substrate and having the chamber shape, the mandrel being arranged and formed, respectively, for being covered by the orifice member and for being thereafter removed and wherein the substrate includes an inlet formed therethrough and into which extends some of the removable mandrel.

2. The assembly of claim 1 further comprising the orifice member that is formed of photoresist material and that substantially covers the mandrel but for an orifice that extends through the orifice member so that the orifice and the chamber are in fluid communication upon removal of the mandrel.

3. The assembly of claim 2 wherein the mandrel is a photosensitive polymer that exhibits differential solubility as compared to the orifice material.

4. The assembly of claim 1 wherein the mandrel is formed of spin-on glass material.

5. The assembly of claim 1 wherein the mandrel may be removed by etching.

6. The assembly of claim 1 wherein the mandrel is metal.

7. The assembly of claim 1 wherein the mandrel is a photoresist material that includes optical dye.

8. A method of producing ultra-small droplets, comprising the step of propelling a droplet from a liquid chamber through an orifice by rapidly heating some of the liquid in the chamber, the droplet having a volume of about 10 femtoliters.

9. The method of claim 8 including the step of sizing the orifice to be about 2 $\mu$m across.

* * * * *

UNITED STATES PATENT AND TRADEMARK OFFICE
CERTIFICATE OF CORRECTION

PATENT NO.    : 6,698,868 B2
DATED         : March 4, 2004
INVENTOR(S)   : Trueba et al.

It is certified that error appears in the above-identified patent and that said Letters Patent is hereby corrected as shown below:

Title page,
Item [56], References Cited, U.S. PATENT DOCUMENTS, please insert the following references:

| | | | |
|---|---|---|---|
| -- 10/003,780 | | Haluzak et al. | |
| 3852563 | 12/1974 | Bohorquez | 347/204 |
| 4438191 | 3/1984 | Cloutier | 430/324 |
| 4809428 | 3/1989 | Aden | 29/611 |
| 4847630 | 7/1989 | Bhaskar | 347/63 |
| 4851371 | 7/1989 | Fisher | 438/21 |
| 4875968 | 10/1989 | O'Neill | 216/27 |
| 4894664 | 1/1990 | Pan | 347/63 |
| 5041190 | 8/1991 | Drake | 438/21 |
| 5160577 | 11/1992 | Deshpande | 216/27 |
| 5194877 | 3/1993 | Lam | 347/63 |
| 5211806 | 5/1993 | Wong | 216/27 |
| 5308442 | 5/1994 | Taub | 216/27 |
| 5306370 | 4/1994 | Herko | 156/155 |
| 5317346 | 5/1994 | Garcia | 347/63 |
| 5851412 | 12/1988 | Kubby | 216/27 |
| 6153114 | 11/2000 | Figueredo | 216/27 |
| 6390606 | 5/2002 | Terui | 347/63 |
| 6204182 | 3/2001 | Truninger | 438/691 |
| 6283582 | 9/2001 | Silverbrook | 347/54 |
| 6241333 | 6/2001 | Wen | 347/15 |
| 6099106 | 8/2000 | Werner | 347/63 |
| 6365058 | 8/2002 | Beatty -- | |

Signed and Sealed this

Thirteenth Day of July, 2004

JON W. DUDAS
*Acting Director of the United States Patent and Trademark Office*